US006668655B2

(12) United States Patent
Harrold et al.

(10) Patent No.: US 6,668,655 B2
(45) Date of Patent: Dec. 30, 2003

(54) ACOUSTIC MONITORING OF FOREIGN OBJECTS IN COMBUSTION TURBINES DURING OPERATION

(75) Inventors: Ronald T. Harrold, Murrysville, PA (US); Zal N. Sanjana, Mt. Lebanon, PA (US); Brian D. Ottinger, Pittsburgh, PA (US); Lawrence L. Ross, Freeport, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 75 days.

(21) Appl. No.: 09/965,715

(22) Filed: Sep. 27, 2001

(65) Prior Publication Data

US 2003/0056595 A1 Mar. 27, 2003

(51) Int. Cl.[7] .......................... G01N 29/10; G01N 29/24
(52) U.S. Cl. ............................................. 73/660; 73/593
(58) Field of Search .................. 73/593, 660, 659, 73/650, 627, 628, 629, 630, 620, 602, 603; 29/889.2, 889.21, 889.23

(56) References Cited

U.S. PATENT DOCUMENTS

| 4,888,948 A | 12/1989 | Fisher et al. |
| 5,070,722 A | 12/1991 | Hawman et al. |
| 5,206,816 A | 4/1993 | Hill et al. |
| 5,445,027 A | 8/1995 | Zorner |
| 5,749,228 A | * 5/1998 | Shiga et al. .................. 416/241 |
| 5,751,219 A | * 5/1998 | Stegmueller ................ 73/866.3 |
| 5,942,690 A | 8/1999 | Shvetsky |
| 6,487,909 B2 | * 12/2002 | Harrold et al. ................ 73/593 |

OTHER PUBLICATIONS

Hoffman, Forrest, "An Introduction to Fourier Theory", http://aurora.phys.utk.edu/∞forrest/papers/fourier/, Sep. 24, 2001, pp. 1–10.

Cowdell, Robert B., "Charts simplify prediction of noise from periodic pulses", Dietronics, Sep. 2, 1968, (7 pgs.) Genisco Technology Corp., Compton, CA.

* cited by examiner

Primary Examiner—Helen Kwok

(57) ABSTRACT

A foreign object impact sensor for use with combustion turbines utilizes a passive acoustic waveguide within the turbine to receive acoustic signals from foreign object impact. The magnitude of these signals is displayed and or stored using a lighted display or other suitable indicating device. The information is also recorded and stored, so that a spectrum signature can be obtained from Fourier analysis.

22 Claims, 5 Drawing Sheets

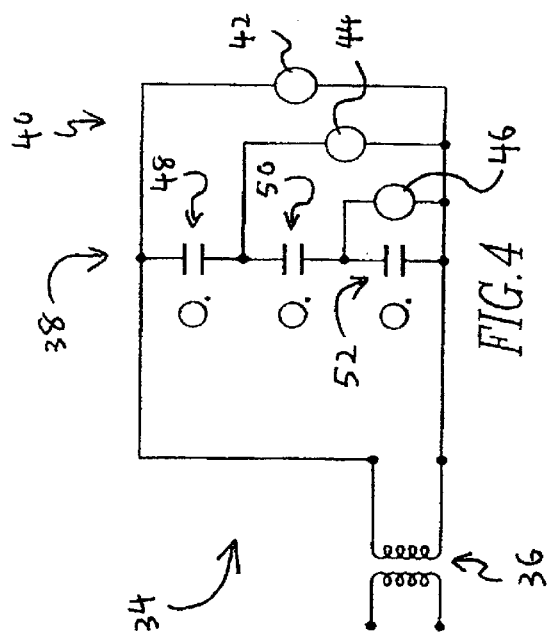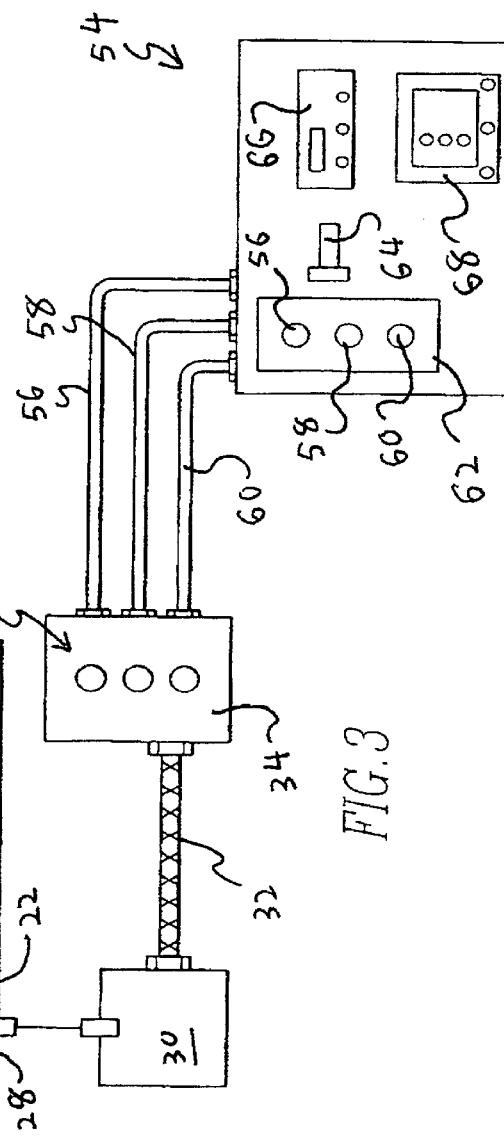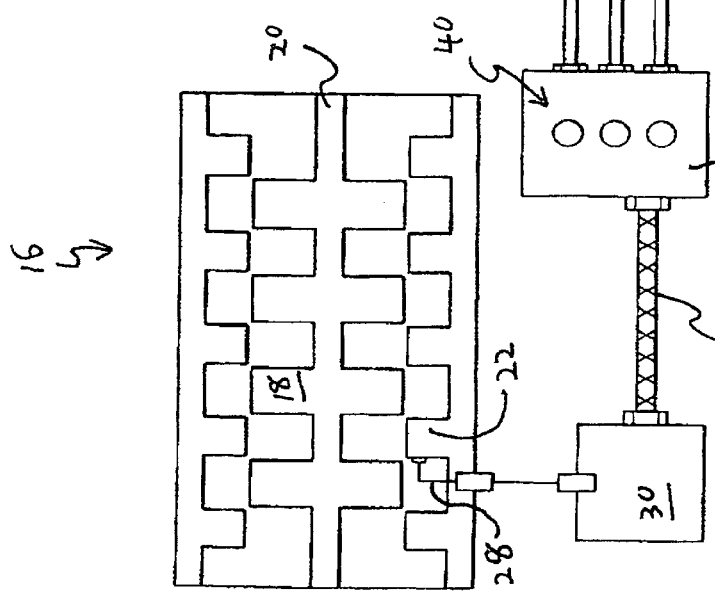

ACOUSTIC MONITORING OF FOREIGN OBJECTS IN COMBUSTION TURBINES DURING OPERATION

BACKGROUND OF THE INVENTION

1. Field of the Invention

The invention relates to on-line monitoring of combustion turbines for defects. More specifically, the invention is an apparatus and method for monitoring acoustic signals within a combustion turbine to monitor the passage of foreign particles through the turbine on-line.

2. Description of the Related Art

Combustion turbines typically operate at extremely high temperatures, for example, 2500° F. to 2900° F. (1371° C. to 1593° C.). Such high temperatures will cause failure of various components unless they are protected from the heat. These components include the rotating blades of the turbine, and the vanes for directing gas flow within the turbine. A typical combustion turbine will have three to four rows each of blades and vanes, with approximately 50 to 100 blades or vanes per row, and will typically have approximately 500 total blades and vanes to protect. A commonly used material for vanes and blades is nickel-cobalt. These components are usually insulated by a thermal barrier coating to enable their use within high temperature environments. A typical thermal barrier coating is yttria-zirconia.

Currently, it is necessary to periodically stop the turbine and inspect the components for deterioration of the thermal barrier coating, defects in other coatings, or other defects, for example, formation of cracks. It would be desirable to monitor the condition of these components while the turbine is in use. Avoiding the need to periodically stop the turbine for inspection reduces downtime, increasing the turbine's efficiency. Similarly, early detection of defects reduces repair costs and outage time, again increasing turbine efficiency. A need exists for monitoring conditions within the turbine that can cause defects, or are a symptom of a defect, such as foreign objects passing through the combustion turbine.

One proposed system for detecting and locating defects within turbine components involves using a probe on the housing of the turbine to measure the acoustic spectrum of the turbine. This acoustic spectrum is then compared with a reference spectrum, with deviations from this reference spectrum indicating a damaged turbine blade or component. Preferred embodiments of this method include generating an acoustic signal to increase the intensity of the acoustic spectrum within the turbine.

Another proposed system is for monitoring synchronous blade vibration. The system includes at least three sensors circumferentially arranged around a row of blades. The sensors may be of the eddy current type, microwave, or optical. The sensors detect the arrival time of each blade at the sensor, using the difference between the expected arrival time of the blade and the actual arrival time of the blade to determine the amplitude of the blade vibration. This information has been analyzed using Fourier transforms to determine the vibratory stress on each blade.

Yet another proposed system for monitoring the condition of a turbine includes mounting an acoustic emission sensor on a surface of an engine component. The sensor will detect the resulting acoustic emissions when particles of debris strike the surface to which it is mounted or other surfaces.

One proposed method utilizes ultrasonic inspection of rotating machinery while the machinery is in operation. The method uses an ultrasonic transducer to radiate pulses of ultrasonic energy at a frequency substantially equal to a subharmonic of the frequency of the turbine rotation. The transducer will sense reflections of the ultrasonic pulses from the blade, and convert the reflections into an electrical signal. Changes in the reflected signal can indicate a damaged blade.

Another system for monitoring the intake of foreign objects into an engine includes sensors positioned near the engine intake and exhaust duct for detecting electrostatic charges induced in the sensors by passing foreign bodies. Each sensor includes a plurality of sensor elements, with each sensor element having an insulating layer of epoxy resin and the charge-collecting layer of silver-loaded epoxy resin.

Accordingly, there is a need for an apparatus and method for detecting the passage of foreign debris through a combustion turbine, measuring the frequency and intensity of the resulting acoustic signals and displaying such information on line, and recording this information, thereby providing an indication of when a turbine needs to be shut down for maintenance.

SUMMARY OF THE INVENTION

The invention is a system for monitoring the frequency and severity of impacts from foreign debris upon various components within a combustion turbine during operation of the turbine. The system relies on the detection of acoustic signals generated by the impact of foreign debris upon various components of the turbine.

An acoustic sensor, such as an acoustic waveguide, is bonded to a suitable location on the combustion turbine. This location may be either inside or outside of the gas turbine, with one example location being adjacent to one of the vanes within the turbine. The other end of the waveguide is bonded to a transducer, for example, a bender transducer, for converting the acoustic signal into an electric signal.

The electrical signal may then be transmitted to a radio frequency step-up transformer for ensuring that even the smallest voltages received are increased to at least approximately 1.5 volts. Lastly, the electrical signal is transmitted to a capacitive voltage divider, transmitting the voltage to one or more light-emitting diodes (LED), depending upon the voltage received. Smaller voltages will light only one LED, whereas larger voltages will light an increasing number of LEDs. For example, a voltage between 1.5 and 2.5 volts may light a green LED, a voltage between 2.5 and 4.5 volts may light a green plus a yellow LED, and a voltage exceeding 4.5 volts may light a green, yellow and red LED.

The received signal may also be recorded for further study using a data logger or a storage oscilliscope. For example, a video camera may record the activation of the LEDs, recording the information on a videocassette, and displaying it on a video screen.

Alternatively, instead of a narrow band [~3 kHz] bender transducer, a wide band [~0.1 to 1 Mhz] transducer may be bonded to the AWG and the acoustic pulse from FOD measured and stored. Once the information is stored, the spectrum signature may be obtained from Fourier analysis. The spectrum signatures from the impact of various objects, such as ceramic chips and metal chips, will be different, allowing for their identification. Certain spectrum signatures, for example, those indicating a chip from a turbine blade, will indicate that it is desirable to shut down the combustion turbine for maintenance.

A sensing system of the present invention can collect and record information about the number and magnitude of foreign object impact within the combustion turbine, and transmit this information over long distances, without power supplies or batteries.

It is therefore an aspect of the present invention to provide a foreign object impact sensor capable of detecting the acoustic signal resulting from a wide variety of foreign objects impacting components within a combustion turbine.

It is another aspect of the present invention to provide a foreign object impact sensor capable of displaying and recording the frequency and severity of foreign object impacts within the combustion turbine.

It is a further aspect of the present invention to provide a foreign object impact sensor providing a means to record and store signals from foreign object impacts, so that a spectrum signature can be obtained from Fourier analysis.

It is another aspect of the present invention to provide a foreign object impact sensor capable of being set up and utilized at minimal cost.

These and other aspects of the invention will become apparent through the following description and drawings.

BRIEF DESCRIPTION OF THE DRAWINGS

FIG. 3 is a schematic diagram illustrating a foreign object impact sensor of the present invention utilized in conjunction with the turbine portion of a combustion turbine.

FIG. 4 is a schematic diagram illustrating the electrical circuitry for providing visual indication of the severity of foreign debris impact within the turbine.

Like reference numbers denote like elements throughout the drawings.

DETAILED DESCRIPTION

The preferred embodiments of the invention is a system for on-line monitoring of foreign object impacts within a combustion turbine. The significance and functioning of the present invention are best understood through a description of the environment within a combustion turbine.

Figure 1:
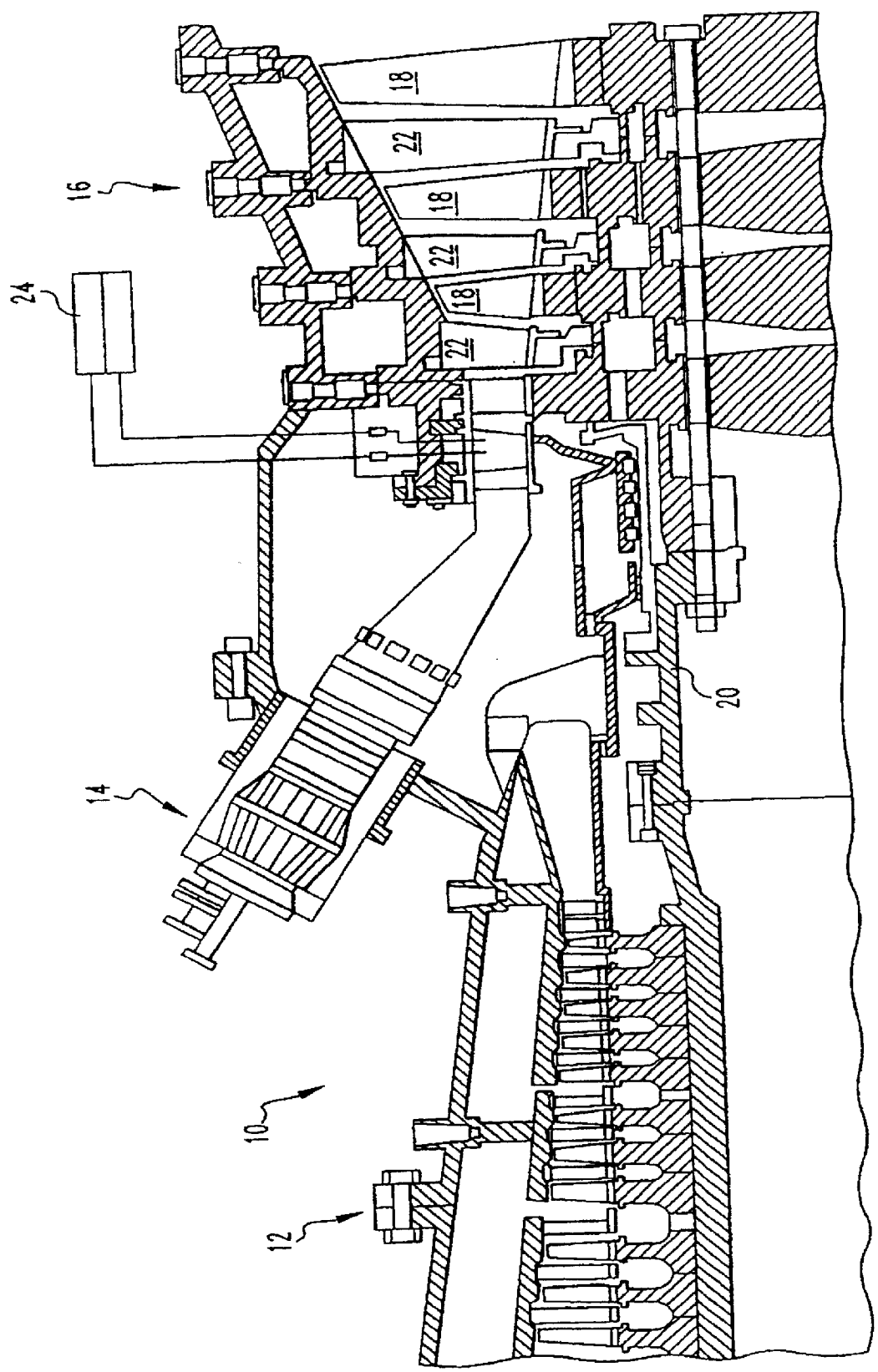
FIG. 1 is a cross-sectional view of a combustion turbine for which the present invention will be used.
Figure 2:
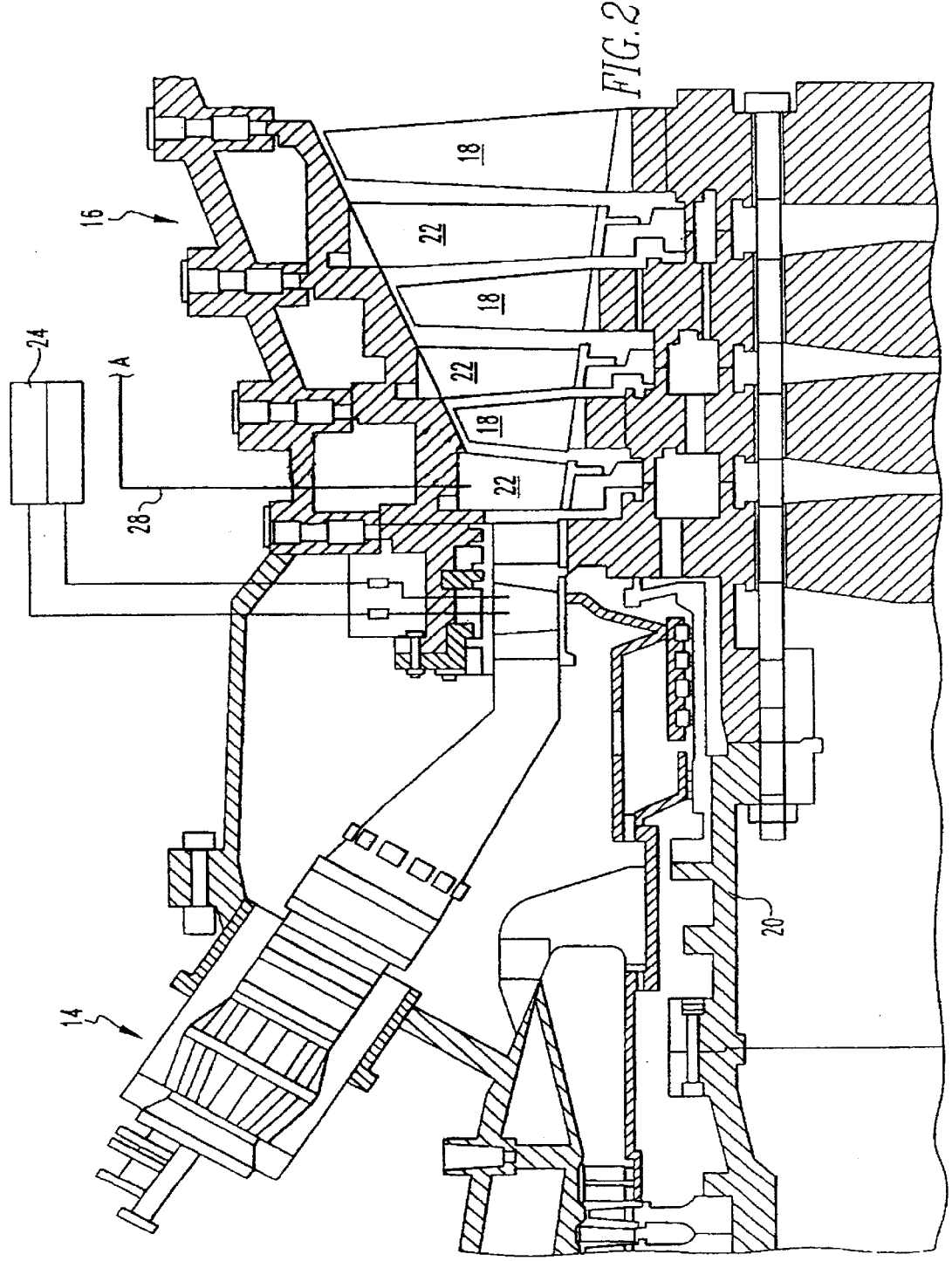
FIG. 2 is a cross-sectional view of the turbine portion of a combustion turbine.

FIGS. 1 and 2 illustrates a combustion turbine 10. The combustion turbine 10 includes a compressor 12, at least one combustor 14, and a turbine 16. The turbine 16 includes a plurality of rotating blades 18, secured to a rotatable central shaft 20. A plurality of stationary vanes 22 are positioned between the blades 18, with the vanes 22 being dimensioned and configured to guide air over the blades 18. The blades 18 and vanes will typically be made from nickel-cobalt, and will typically be coated with a thermal barrier coating, for example yttria-zirconia.

In use, air is drawn in through the compressor 12, where it is compressed and driven towards the combustor 14. The combustor 14 mixes the air with fuel and ignites it, thereby forming a working gas. This working gas will typically be approximately 2500° F. to 2900° F. (1371° C. to 1593° C.). This gas expands through the turbine 16, being guided across the blades 18 by the vanes 22. As the gas passes through the turbine 16, it rotates the blades 18 and shaft 20, thereby transmitting usable mechanical work through the shaft 20. The combustion turbine 10 also includes a cooling system 24, dimensioned and configured to supply a coolant, for example steam or compressed air, to the blades 18 and vanes 22.

From the above description, it becomes apparent that the environment within the combustion turbine 10 is particularly harsh, and is therefore likely to cause various forms of component deterioration, such as deterioriation of thermal barrier coatings and coatings for corrosion prevention, or formation of cracks within varying components. Any such deterioration has the potential for causing fragments from various coatings or underlying components to be broken off, striking other surfaces within the combustion turbine as they are blown through the turbine. Additionally, there may also be some potential for foreign objects to be sucked into the compressor portion of the turbine, traveling throughout the turbine and striking various surfaces along the way. Monitoring the acoustic signals generated by these foreign object impacts, thereby determining the frequency and severity of the impacts, permits a determination of when the combustion turbine must be stopped and serviced.

Referring to FIGS. 2–3, means for receiving acoustic signals within the combustion turbine, which is preferably an acoustic waveguide 28, is illustrated. The acoustic waveguide 28 may be bonded to any surface inside or outside the combustion turbine 10, and in the present example is illustrated bonded to a vane 22. Preferred materials for such an acoustic waveguide are nichrome, platinum, and/or tungsten and suitable alloy of such materials, with the specific material chosen for it's acoustic as well as temperature resistant properties. A special feature of acoustic waveguides is that they can be bonded to various surfaces by either a point or direct contact or by bonding a few inches of acoustic waveguide length to the surface edges, or other flat surfaces to a vane. Such bonding can be achieved by welding or brazing.

Referring to FIG. 3, the acoustic waveguide 28 is attached to an acoustic receiver 30, which is preferably a piezoceramic crystal. One example of such an acoustic receiver is a bender transducer or bender acoustic sensor. Such acoustic receivers convert acoustic signals into electrical signals. Depending on the sensitivity required, the acoustic receiver 30 may include only a single piezoceramic crystal, or alternatively, may include a plurality of piezoceramic crystals each being bonded sequentially to a plurality of acoustic waveguides 28. If multiple piezoceramic crystals are utilized, each crystal will preferably have a different resonant frequency. For example, crystals with frequencies of 10 kHz, 30 kHz, 60 kHz, 90 kHz, 120 kHz, and 240 kHz. If only a single crystal is used, an example of a suitable resonant frequency for the crystal is 3 kHz. The use of single 3 kHz acoustic bender sensor has the advantage of producing a large terminal voltage from impact pressure signals, whereas the use of multiple bender sensors has the advantage of permitting the identification of spectrum signatures across a wide range of frequencies for each type of particle impact. The acoustic receiver 30 is connected by an electrical lead 32 to a signal display apparatus 34.

Referring to FIGS. 3–4, the signal display apparatus 34 and its various components are illustrated. Because it is anticipated that most electrical signals coming from the acoustic receiver 30 will be in the 100 to 300 mV range, displaying this signal may be facilitated by using a step-up radio frequency transformer 36 to increase the signal's voltage. The step-up transformer 36 may preferably increase this electrical signal to a value exceeding 1.5 volts, which is sufficient to momentarily light a light emitting diode. This electrical signal may then be transmitted through a capacitive voltage dividing network 38 to a lighted display 40. The lighted display 40 includes a plurality of light-emitting diodes for displaying the frequency and severity of foreign object impacts, with the present example having three light-emitting diodes: a green LED 42, a yellow LED 44, and a red LED 46. The capacitive voltage divider 38 likewise includes a plurality of capacitors connected in series, dimensioned and configured to light an increasing number of the LEDs 42, 44, 46 with increasing voltage signals. In the present example, a signal greater than 1.5 volts will light the green LED 42, a signal exceeding 2.5 volts will light the green LED 42 and yellow LED 44, and a signal exceeding 4.5 volts will light the green LED 42, yellow LED 44, and red LED 46. Referring specifically to FIG. 4, this is accomplished by electrically connecting the green LED 42 with the transformer 36 so that all three capacitors 48, 50, 52, are by-passed. Expressed differently, the green LED 42 and capacitive voltage divider 38 are electrically connected in parallel. The yellow LED 44 is electrically connected in series with the capacitor 48, and in parallel with the capacitors 50 and 52. Likewise, the red LED 46 is electrically connected in series with the capacitors 48 and 50, and in parallel with the capacitor 52.

Referring back to FIG. 3, the magnitude and severity of the foreign object impacts may additionally be displayed and recorded at a remote display apparatus 54. A plurality of optical fiber lightguides 56, 58, 60, with each optical fiber lightguide 56, 58, 60 corresponding to one LED 42, 44, 46, may transmit the light generated by the LEDs 42, 44, 46 to be displayed. The remote display apparatus 54 may also include a TV camera 64 for recording the lighted display 62, a video cassette recorder 66 for maintaining a historical record of the frequency and severity of foreign object impacts, and a video monitor 68 for viewing the frequency and severity of past or present foreign object impacts.

The acoustic monitoring system of the present invention provides several advantages. Because the initial source of energy for the system is the acoustic wave generated by the foreign object impact within the combustion turbine 10, the magnitude and severity of these foreign object impacts may be converted to a lighted display without power supplies or batteries. Either the electrical lead 32 or the optical fiber lightguides 56, 58, 60 may transmit the appropriate signals over long distances, thereby permitting remote monitoring of the combustion turbine 10. Additionally, the frequency and severity of foreign object impacts may be recorded for further study.

Figure 5:
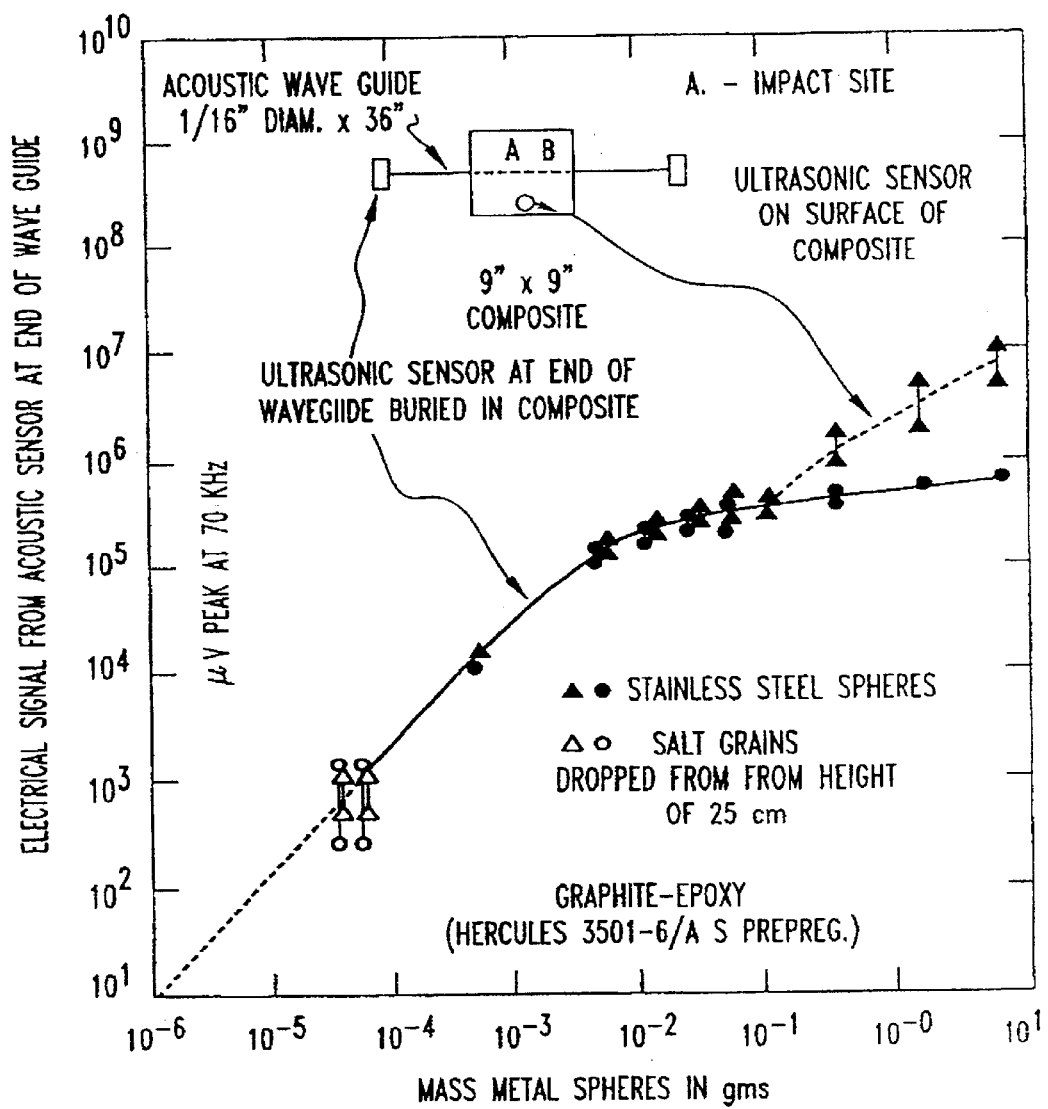
FIG. 5 is a graph illustrating the expected acoustic signals resulting from various debris impacting various surfaces.

FIG. 5 illustrates the resulting electrical signal from utilizing an acoustic waveguide to detect the impact of various particles on various surfaces and then converting the acoustical signal into an electrical signal. One surface utilized in developing the information displayed in FIG. 5 was a graphite-epoxy composite. Various masses of metal spheres and salt grains were dropped onto this surface, and the resulting acoustic waves were detected using an epoxy-fiberglass acoustic waveguide. In this experiment, the signal received from the impact of salt grains having a mass less than $10^{-4}$ grams was in the range 300–1,200 $\mu$V range and the signal received from the impact of a 1 gram metal sphere exceeded 100 mV. Switching to nichrome acoustic waveguide bonded to a gas turbine blade, and dropping salt grains on this blade, resulted in electrical signals in the range of 500 $\mu$V. Although this experiment differs from the environment within a combustion turbine in that a combustion turbine will produce background noise corresponding to some of the resonant frequencies of some of the piezoceramic crystals utilized as acoustic receivers, it is expected that acoustic signals from foreign object impacting on various surfaces will produce momentary signals higher than the background noise.

Figure 6:
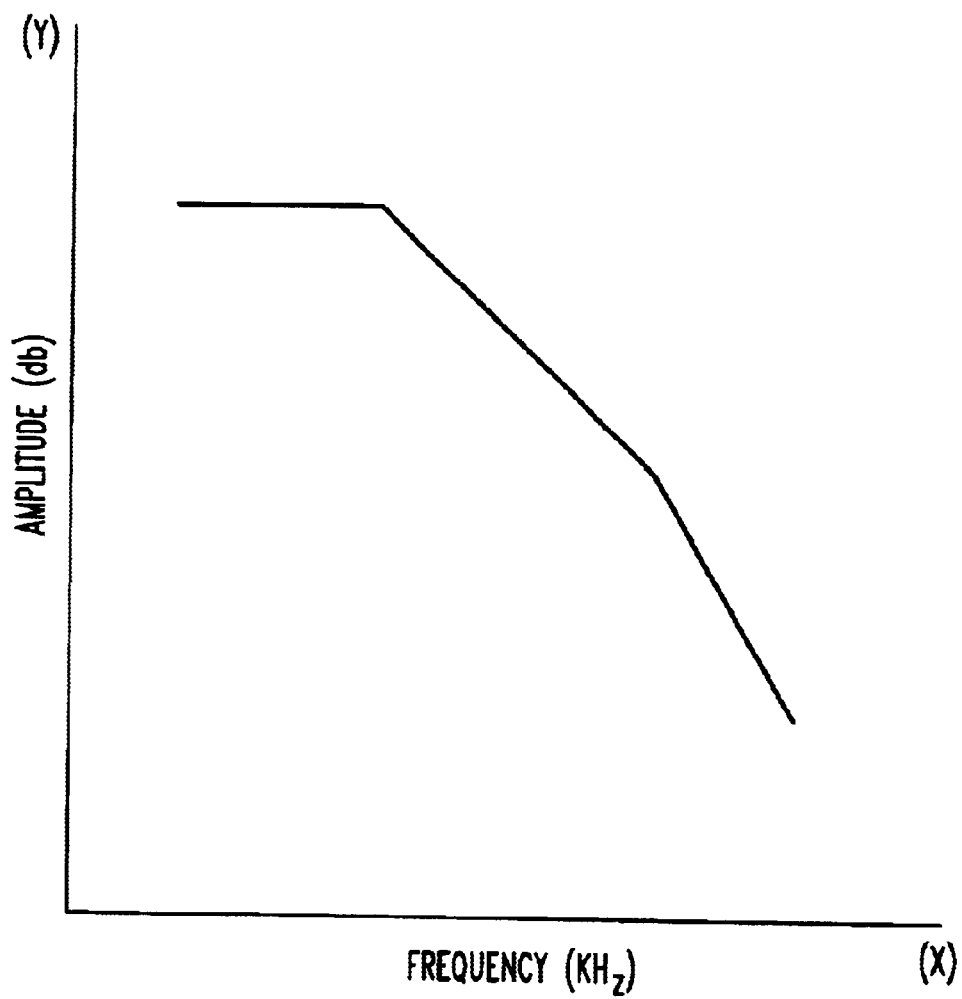
FIG. 6 is an example of a spectrum signature produced by a plurality of acoustic waves at various frequencies.

In addition to recording and studying the visual display resulting from the foreign object impact, the frequency and severity of these impacts may be studied using Fourier analysis to obtain the spectrum signature for a plurality of impacts. Use of Fourier analysis requires the use of either a single, wide spectrum piezoceramic crystal, or a plurality of piezoceramic crystals having different resonant frequencies, as the acoustic receiver 30. Fourier analysis is well known in the art of signal processing. Fourier analysis permits the determination and display of the proportion to which each different frequency within the entire spectrum generated by the foreign object impact contributes to the overall spectrum signature. FIG. 6 is one example of such a spectrum signature for a plurality of waves. In the example of FIG. 6, a low proportion of the overall spectrum signature is produced by high frequency waves, and a high proportion of the overall spectrum signature is produced by low frequency waves. A foreign object impact against a surface within the combustion turbine 10 will produce acoustic waves over a range of frequencies, with the proportional contribution of each frequency to the overall spectrum signature varying based on the type of foreign object and type of surface impacted. Therefore, the specific nature of the foreign object impact can be determined by comparing the spectrum signatures generated with the known spectrum signatures of various foreign object impacts. For example, a foreign object impact generating the signature spectrum of a piece of a turbine blade 18 striking a surface within the combustion turbine 10 may serve as an indication that it is necessary to shut down the combustion turbine 10 for maintenance.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A system for monitoring acoustic signals generated within a combustion turbine, the combustion turbine having an interior portion, said system comprising:

an acoustic waveguide adapted to be located within acoustic communication with the combustion turbine's interior portion;

an acoustic receiver in communication with said acoustic waveguide, said acoustic receiver being adapted to produce an electrical signal having a voltage in response to receipt of an acoustic signal;

a transformer adapted to increase said voltage of said electrical signal from said acoustic receiver sufficiently to light a light-emitting device;

a voltage divider network electrically connected to said transformer;

a plurality of light-emitting devices electrically connected to said voltage divider network;

said voltage divider network being adapted to provide an electrical current to an increasing number of light emitting devices with increasing voltage received at said voltage divider network; and the system being adapted to receive the electrical power necessary for providing the electrical current to the light emitting devices from receiving the acoustic signals generated within the combustion turbine, and converting the acoustic signals to electrical signals.

2. The system according to claim 1, wherein said acoustic waveguide is made of a material adapted to withstand high temperatures.

3. The system according to claim 2, wherein said acoustic waveguide is made from a material having property characteristics that resists the environment elements and provide acoustic transmission.

4. The system according to claim 2, wherein said acoustic waveguide is made from a material selected from the group consisting of nichrome, platinum, and tungsten.

5. The system according to claim 1, wherein said acoustic receiver includes at least one piezoceramic crystal or bender transduscer.

6. The system according to claim 5, wherein said acoustic receiver includes a wideband piezoceramic crystal or bender transducer.

7. The system according to claim 5, wherein said acoustic receiver includes a plurality of piezoceramic crystals or bender transducer, with each of said piezoceramic crystals or bender transducer having a different resonant frequency.

8. The system according to claim 1, wherein said voltage divider network is a capacitive voltage divider.

9. The system according to claim 1, further comprising a video camera operatively connected to a videocassette recorder, said video camera and videocassette recorder being adapted to record said light emitting devices.

10. The system according to claim 1, further comprising means for obtaining a spectrum signature of the acoustic signals received.

11. The system according to claim 1, further comprising means for remote monitoring of said acoustic signals.

12. A system for monitoring acoustic signals generated within a combustion turbine, the combustion turbine having an interior portion, said system comprising:

means for receiving an acoustic signal generated within a combustion turbine;

means for converting said acoustic signal into an electrical signal, the electrical signal having a voltage;

means for visually displaying the magnitude and frequency of said electrical signal; and the system being adapted to receive the electrical power necessary for visually displaying the magnitude and frequency of said electrical signal from receiving the acoustic signals generated within the combustion turbine, and converting the acoustic signals to electrical signals.

13. The system according to claim 12, wherein said means for receiving an acoustic signal include an acoustic waveguide adapted to be located within acoustic communication with the combustion turbine's interior portion.

14. The system according to claim 12, wherein said means for converting said acoustic signal into an electrical signal include at least one piezoceramic crystal.

15. The system according to claim 14, wherein said means for converting said acoustic signal into an electrical system includes a wideband piezoceramic crystal.

16. The system according to claim 14, wherein said means for converting said acoustic signal into an electrical signal includes a plurality of piezoceramic crystals, with each of said piezoceramic crystals having a different resonant frequency.

17. The system according to claim 12, wherein said means for visually displaying said magnitude and frequency of said electrical signal include:

a transformer adapted to increase said voltage of said electrical signal from said means for converting said acoustic signal into an electrical signal sufficiently to light a light-emitting device;

a voltage divider network electrically connected to said transformer;

a plurality of light-emitting devices electrically connected to said voltage divider network; and said voltage divider network being adapted to provide an electrical current to a data acquisition device to display or record increased voltage received at said voltage divider network.

18. The system of claim 17 wherein the data acquisition device comprises an increasing number of light emitting devices to display the increasing voltage received at said voltage divider network.

19. The system according to claim 17, wherein said voltage divider network is a capacitive voltage divider.

20. The system according to claim 17, further comprising means for recording and storing a magnitude and frequency of occurrence of said acoustic signals.

21. The system according to claim 12, further comprising means for obtaining a spectrum signature of the acoustic signals received.

22. The system according to claim 12, further comprising means for remote monitoring of said acoustic signals.

* * * * *